United States Patent [19]

Souda et al.

[11] Patent Number: 5,075,335

[45] Date of Patent: Dec. 24, 1991

[54] GUANIDINOBENZOIC ESTER DERIVATIVE

[75] Inventors: Shigeru Souda, Ushiku; Naoyuki Shimomura, Ibaraki; Norihiro Ueda, Ibaraki; Shuhei Miyazawa, Ibaraki; Takashi Yamanaka, Ibaraki; Kaname Miyamoto, Ibaraki; Ieharu Hishinuma, Moriyamachi; Junichi Nagakawa; Naoko Nagaoka, both of Ibaraki; Hidetoshi Kawashima, Toride; Tsutomu Kawata, Tsuchiura; Junsaku Nagaoka, Ibaraki; Tsuneo Wakabayashi, Mito, all of Japan

[73] Assignee: Eisai Co., Ltd., Tokyo, Japan

[21] Appl. No.: 495,444

[22] Filed: Mar. 16, 1990

Related U.S. Application Data

[62] Division of Ser. No. 225,278, Jul. 28, 1988, Pat. No. 4,948,808, which is a division of Ser. No. 946,458, Dec. 24, 1986, Pat. No. 4,801,603.

Foreign Application Priority Data

Dec. 27, 1985 [JP] Japan .................. 60-293268

[51] Int. Cl.$^5$ .................. A01N 37/12; A01N 31/24
[52] U.S. Cl. .................. 514/535; 514/540; 514/634; 546/220; 548/473; 548/478; 548/547; 560/34; 564/104; 568/77
[58] Field of Search .............. 514/535, 425, 540, 634; 560/34; 548/547, 473, 478; 546/404; 564/104; 568/77

[56] References Cited

PUBLICATIONS

Choay et al., Chemical Abstracts, vol. 95, 1981 p. 639, :132533x.

*Primary Examiner*—Jose G. Dees
*Assistant Examiner*—Deborah D. Carr
*Attorney, Agent, or Firm*—Flynn, Thiel, Boutell & Tanis

[57] ABSTRACT

A guanidinobenzoic ester derivative having the formula is novel and effective to inhibit enzymes such as trypsin, plasmin and thrombin, being useful for treatment of the pancreatitis and hemorrhagic disease and thrombosis.

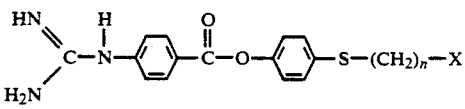

wherein X represents a group of the formula:

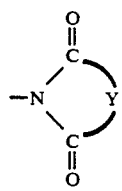

in which Y is a group of the formula: $-(CH_2)_m-$, m being an integer of 2 or 3,

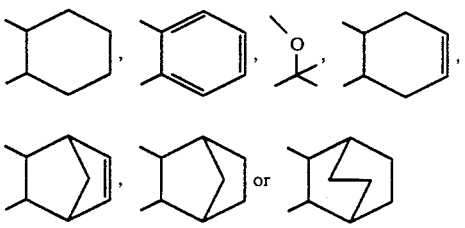

or a group of the formula:

—OR in which R is a hydrogen atom or a lower alkyl group, and n represents an integer of 1 to 5.

11 Claims, No Drawings

GUANIDINOBENZOIC ESTER DERIVATIVE

This is a division of Ser. No. 07/225 278, filed July 28, 1988, now U.S. Pat. No. 4,948,508 which is a division of Ser. No. 06/946 458, filed Dec. 24, 1986, now U.S. Pat. No. 4,801,603.

The invention relates to a guanidinobenzoic ester derivative, a process for preparing the compound, a pharmaceutical composition containing the same, and a method for treating a special disease with the compound.

STATEMENT OF PRIOR ART

Pancreatitis is clinically divided into acute pancreatitis and chronic pancreatitis. When the causes or factors of acute pancreatitis are removed, the pancreas recovers from the illness into a normal state both clinically and biologically. On the other hand even when the causes or factors thereof of chronic pancreatitis are eliminated, the histological and functional disorders still remain. Though the causes of pancreatitis have not fully been understood, the number of patients of alcoholic pancreatitis is the largest followed by those of ill-defined (idiopathic) pancreatitis and cholelithiasic pancreatitis in Japan.

The process from the initial stage to the crisis stage of pancreatitis is complicated and has not been fully understood. Antienzymatic therapy is employed frequently as a pharmacotherapy at present and the further developmetn of a pancreatic enzyme inhibitor having a higher safety and better effects is demanded.

SUMMARY OF THE INVENTION

An object of the present invention is to provide new guanidinobenzoic ester derivatives. Another object of the invention is to provide a process for producing said guanidinobenzoic ester derivatives. Still another object of the invention is to provide medicines containing as an active ingredient said guanidinobenzoic ester derivative.

The intended compounds of the present invention are guanidinobenzoic ester derivatives of the following general formula (I) and pharmacologically allowable salts thereof:

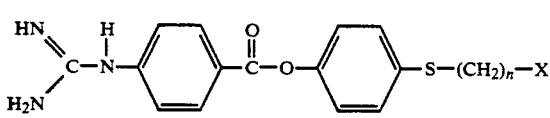

wherein X represents a group of the formula:

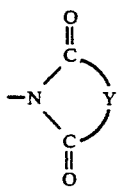

in which Y is a group of the formula: $-(CH_2)_m-$, m being an integer of 2 or 3,

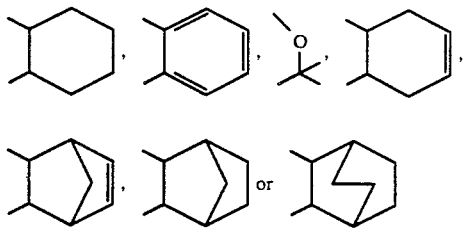

or a group of the formula:

$-OR$ in which R is a hydrogen atom or a lower alkyl group, and n represents an integer of 1 to 5.

The lower alkyl groups in the above definition of R are straight chain or branched alkyl groups having 1 to 6 carbon atoms such as methyl, ethyl, n-propyl, n-butyl, isopropyl, isobutyl, 1-methylpropyl, tert-butyl, n-pentyl, 1-ethylpropyl, isoamyl and n-hexyl groups.

Examples of the pharmacologically acceptable salts include inorganic acid addition salts such as hydrochlorides, sulfates, hydrobromides, perchlorates and hydriodides and organic acid addition salts such as oxalates, maleates, fumarates, succinates and methanesulfonates.

The compounds (I) and pharmacologically allowable salts of them according to the present invention have a strong inhibiting effect on enzymes such as trypsin, plasmin and thrombin and, therefore, they can be used as trypsin inhibitors effective for the treatment of pancreatitis, plasmin inhibitors effective for the treatment of hemorrhagic diseases and thrombin inhibitors effective for the treatment of thrombosis.

Process for Preparing the Compound of this Invention

The compounds (I) of the present invention can be produced be various processes. Typical examples of them will now be described.

The intended compounds of the present invention can be obtained by esterifying a guanidinobenzoic acid of the following formula (II):

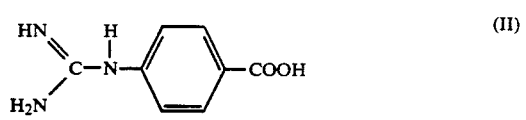

with a compound of the general formula (III):

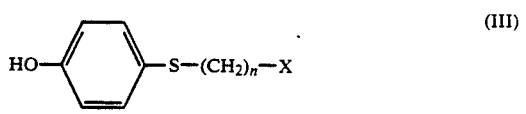

wherein X and n are as defined above, in an ordinary manner. In the most typical process, guanidinobenzoic acid of the above formula (II) or its reactive derivative is esterified with the compound of the above general formula (III). More particularly, the intended compound (I) of the present invention can be obtained by reacting a halide of guanidinobenzoic acid (II), i.e. a compound of the following formula (II'), obtained easily by, for example, heating the compound (II) together with thionyl chloride:

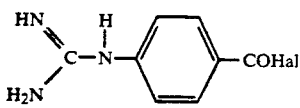
(II')

wherein Hal represents a halogen atom such as chlorine or bromine, with the compound (III) in the presence of an acid-binding agent such as pyridine or triethylamine. Examples of organic solvents usable in this process include tetrahydrofuran, ether, benzene, toluene, dimethylformamide, pyridine and dimethyl sulfoxide. Among them, pyridine is the most preferred. When using an organic solvent other than pyridine, an organic amine such as triethylamine, tributylamine, dimethylamine or pyridine or an inorganic base such as calcium carbonate, sodium carbonate or sodium hydroxide may be used as the acid-binding agent.

In another process, guanidinobenzoic acid of the above formula (II) is directly condensed with a compound of the formula (III) in the presence of a dehydrating agent such as DCC (1,3-dicyclohexylcarbodiimide).

When X in the above formula (I) represents —OH in both of the above-mentioned processes, a compound of the general formula (III'):

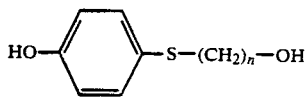
(III')

is used as the compound (III). In such a case, the hydroxyl group bonded with the alkylene is protected with a protective group used in an ordinary chemical reaction in the course of the reaction and the protective group is removed from the hydroxyl group after completion of the reaction. Typical examples of the protective groups include benzyl, p-methoxybenzyl, 3,4-dimethoxybenzyl, triphenylmethyl, methoxymethyl, methylthiomethyl, 2-methoxyethoxymethyl, tetrahydropyranyl and tetrahydrothiopyranyl groups.

The compounds (I) obtained by the above-mentioned processes can be suitably converted into pharmacologically allowable acid addition salts by ordinary process.

In one embodiment, the obtained compound (I) is treated with an aqueous sodium hydrocarbonate solution to form a carbonate and, if necessary, the carbonate can be converted easily into a salt with an inorganic acid such as hydrochloric, sulfuric, phosphoric, hydrobromic or nitric acid or an organic acid such as formic, acetic, lactic, tartaric, oxalic, citric, succinic, fumaric, maleic, methanesulfonic, benzenesulfonic or toluenesulfonic acid.

The starting compounds (III) used in the above-mentioned process can be prepared by, for example, the following process:

(i) when X in the formula (I) represents a group of the formula:

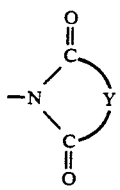

in which Y is as defined above, and n represents an integer of 2 to 5:

step 1

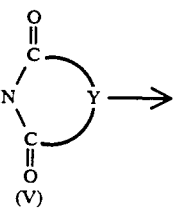

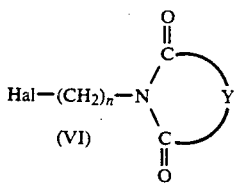

in which Hal is a halogen atom and n and Y are as defined above.

A 1, n-dihalogenoalkane (IV) in which the halogen is preferably bromine or chlorine is condensed with an imide compound of the formula (V) in the presence of a base such as potassium carbonate, sodium carbonate, sodium hydroxide or potassium hydroxide to obtain a compound of the formula (VI). This reaction is carried out in an organic solvent such as acetone, methyl ethyl ketone, methyl isobutyl ketone, methanol, ethanol, propanel, isopropanel, butanol, and dimethylformamide (DMF) of dimethyl sulfoxide (DMSO).

step 2

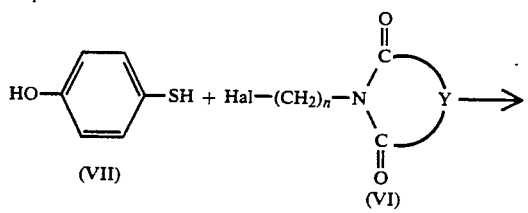

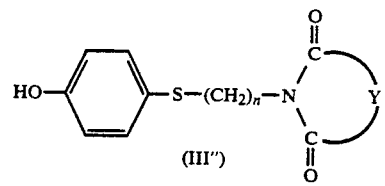

in which n and Y are as difined above.

The compound (VI) obtained in step 1 is condensed with 4-hydroxythiophenol of the formula (VII) in the presence of a base such as potassium carbonate, sodium carbonate, sodium hydrocarbonate, sodium hydroxide or potassium hydroxide to obtain a compound (III''). This reaction is carried out in an organic solvent such as methanol, ethanol, propanol, isopropanol, butanol, acetone, methyl ethyl ketone, methyl isobutyl ketone, dimethylformamide (DMF) or dimethyl sulfoxide (DMSO).

(ii) To obtain a compound of the formula (I) wherein X represents a group of the formula:
ti —OR
in which R is a lower alkyl group, a compound of the general formula:

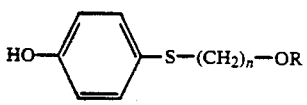

is used as the starting compound. This compound can be produced by, for example, a process disclosed in the specification of Japanese Patent Publication No. 179/1967.

(iii) When n in the formula (I) is 1, the following process can be employed:

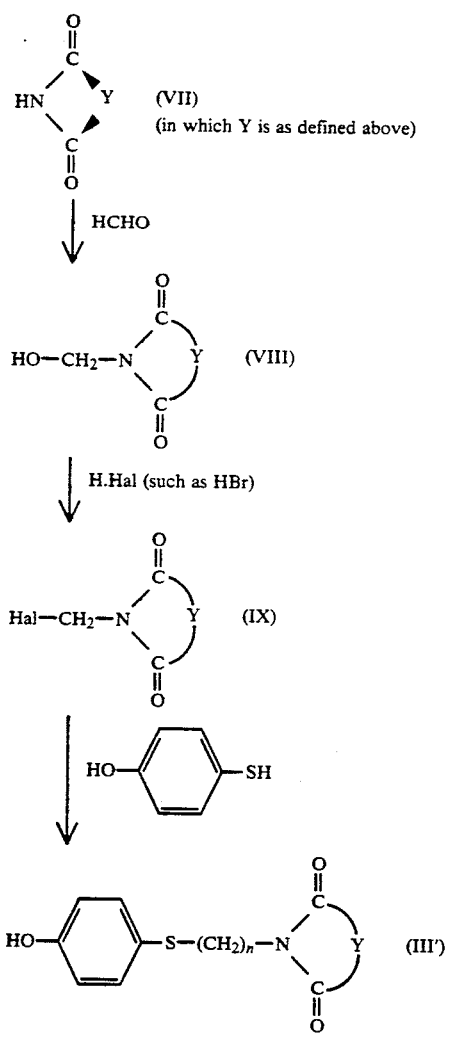

Typical examples of the compounds of the present invention will be given below to facilitate understanding of the present invention, which by no means limit the invention:

4-(3-phthalimidopropylthio)phenyl 4-guanidinobenzoate 4-(4-phthalimidobutylthio)phenyl 4-guanidinobenzoate, 4-(5-phthalimidopentylthio)phenyl 4-guanidinobenzoate, 4-[3-(cis-1,2-cyclohexanedicarboxyimido)propylthio]phenyl 4-guanidinobenzoate, 4-[4-(cis-1,2-cyclohexanedicarboxyimido)butylthio]phenyl 4-guanidinobenzoate, 4-[5-(cis-1,2-cyclohexanedicarboxyimido)pentylthio]phenyl 4-guanidinobenzoate, 4-[3-(5,5-dimethyl-2,4-dioxooxazolidin-3-yl)propylthio]phenyl 4-guanidinobenzoate, 4-[4-(5,5-dimethyl-2,4-dioxooxazolidin-3-yl)butylthio]phenyl 4-guanidinobenzoate, 4-[5-(5,5-dimethyl-2,4-dioxooxazolidin-3-yl)pentylthio]phenyl 4-guanidinobenzoate, 4-(3-hydroxypropylthio)phenyl 4-guanidinobenzoate, 4-(4-hydroxybutylthio)phenyl 4-guanidinobenzoate, 4-(5-hydroxypentylthio)phenyl 4-guanidinobenzoate, 4-(3-ethoxypropylthio)phenyl 4-guanidinobenzoate, 4-(4-ethoxybutylthio)phenyl 4-guanidinobenzoate, 4-(5-ethoxypentylthio)phenyl 4-guanidinobenzoate, 4-(2-methoxyethylthio)phenyl 4-guanidinobenzoate, 4-(3-methoxypropylthio)phenyl 4-guanidinobenzoate, 4-(4-methoxybutylthio)phenyl 4-guanidinobenzoate, 4-(5-methoxypentylthio)phenyl 4-guanidinobenzoate, 4-(2-isopropoxyethylthio)phenyl 4-guanidinobenzoate, 4-(3-isopropoxypropylthio)phenyl 4-guanidinobenzoate, 4-(4-isopropoxybutylthio)phenyl 4-guanidinobenzoate, 4-(5-isopropoxypentylthio)phenyl 4-guanidinobenzoate, 4-(succinimidomethylthio)phenyl 4-guanidinobenzoate, 4-(phthalimidomethylthio)phenyl 4-guanidinobenzoate, 4-[(cis-1,2-cyclohexanedicarboxyimido)methylthio]phenyl 4-guanidinobenzoate, 4-[(5,5-dimethyl-2,4-dioxooxazolidin-3-yl)methylthio]phenyl 4-guanidinobenzoate, 4-(glutarimidomethylthio)phenyl 4-guanidinobenzoate, 4-(2-glutarimidoethylthio)phenyl 4-guanidinobenzoate, 4-(3-glutarimidopropylthio)phenyl 4-guanidinobenzoate, 4-(4-glutarimidobutylthio)phenyl 4-guanidinobenzoate, 4-(5-glutarimidopentylthio)phenyl 4-guanidinobenzoate, 4-(2-succinimidoethylthio)phenyl 4-guanidinobenzoate, 4-(2-hydroxyethylthio)phenyl 4-guanidinobenzoate, 4-(2-ethoxyethylthio)phenyl 4-guanidinobenzoate, 4-(2-phthalimidoethylthio)phenyl 4-guanidinobenzoate, 4-(3-succinimidopropylthio)phenyl 4-guanidinobenzoate, 4-(4-succinimidobutylthio)phenyl 4-guanidinobenzoate, 4-(5-succinim.idopentylthio)phenyl 4-guanidinobenzoate, 4-[2-(cis-1,2-cyclohexanedicarboxyimido)ethylthio]phenyl 4-guanidinobenzoate, 4-[2-(5,5-dimethyl-2,4-dioxooxazolidin-3-yl)-ethylthio]phenyl 4-guanidinobenzoate, 4-[2-(cis-bicyclo[2,2,1]heptane-endo-2,3-dicarboxyimido)ethylthio]phenyl 4-guanidinobenzoate, 4-[2-(cis-bicyclo[2,2,2]octane-2,3-dicarboxyimido)ethylthio]phenyl 4-guanidinobenzoate, 4-[2-(cis-bicyclo[2,2,1]hept-5-ene-endo-2,3-dicarboxyimido)ethylthio]phenyl 4-guanidinobenzoate, and 4-[2-(cis-1,2,3,6-tetrahydrophthalimido)ethylthio]-phenyl 4-guanidinobenzoate.

The following experiments will prove the pharmacological effects of the compounds of the present invention.

PHARMACOLOGICAL EXPERIMENTS

The effects of typical compounds of the present invention in inhibiting trypsin, plasmin and thrombin in vitro were examined. The trypsin-inhibiting effect was represented in terms of a molar concentration of the compound which inhibits the activity of 0.5 μg/ml of trypsin to hydrolyze benzoyl-D,L-arginine-p-nitroanilide hydrochloride by 50% at 25° C. In the determination of the plasmin- and thrombin-inhibiting effects, 50% inhibitory concentrations were determined by using H-D-Val-Leu-L-Lys-p-nitroanilide dihydrochloride and H-D-Phe-L-pipecolyl-L-Arg-p-nitroanilide dihydrochloride, respectively, as the substrate.

The results are shown in Table 1

TABLE 1

| Compound | 50% Inhibitory concentration (IC$_{50}$) (M) | | |
|---|---|---|---|
| | Trypsin | Plasmin | Thrombin |
| A | $4.3 \times 10^{-8}$ | $1.3 \times 10^{-6}$ | $2.5 \times 10^{-7}$ |
| B | $4.7 \times 10^{-8}$ | $9.5 \times 10^{-7}$ | $5.3 \times 10^{-7}$ |
| C | $4.5 \times 10^{-8}$ | $2.2 \times 10^{-6}$ | $3.5 \times 10^{-7}$ |
| D | $5.9 \times 10^{-8}$ | $1.3 \times 10^{-6}$ | $4.2 \times 10^{-7}$ |
| E | $2.2 \times 10^{-8}$ | $2.3 \times 10^{-6}$ | $5.7 \times 10^{-7}$ |
| F | $3.4 \times 10^{-8}$ | $6.4 \times 10^{-7}$ | $2.7 \times 10^{-7}$ |
| G | $6.2 \times 10^{-8}$ | $1.0 \times 10^{-6}$ | $1.6 \times 10^{-7}$ |
| H | $3.0 \times 10^{-8}$ | $9.2 \times 10^{-7}$ | $1.1 \times 10^{-7}$ |
| I | $5.5 \times 10^{-8}$ | $8.3 \times 10^{-7}$ | $3.2 \times 10^{-7}$ | compound A: (4-(2-hydroxyethylthio)phenyl 4-guanidinobenzoate methanesulfonate,
compound B: 4-(2-succinimidoethylthio)phenyl 4-guanidinobenzoate methanesulfonate,
compound C: 4-(2-ethoxyethylthio)phenyl 4-guanidinobenzoate methanesulfonate,
compound D: 4-(3-succinimidopropylthio)phenyl 4-guanidinobenzoate methanesulfonate,
compound E: 4-(4-succinimidobutylthio)phenyl 4-guanidinobenzoate methanesulfonate,
compound F: 4-(5-succinimidopentylthio)phenyl 4-guanidinobenzoate methanesulfonate,
compound G: 4-[2-(cis-1,2-cyclohexanedicarboxyimido)-ethylthio]phenyl 4-guanidinobenzoate methanesulfonate,
compound H: 4-(2-phthalimidoethylthio)phenyl 4-guanidinobenzoate methanesulfonate, and
compound I: 4-[2-(5,5-dimethyl-2,4-dioxooxazolidin-3-yl)ethylthio]phenyl 4-guanidinobenzoate methanesulfonate.

It is apparent from the results of the above experiments that the compounds of the present invention have a strong inhibitory effect against enzymes such as trypsin, plasmin and thrombin.

The compounds A to I used in the above experiments were subjected to acute toxicity tests by administration to ICR mice by intravenous injection. These compounds had an LD$_{50}$ in the range of 50 to 200 mg/kg.

Thus, the compounds of the present invention have excellent inhibiting effects on enzymes such as trypsin, plasmin and thrombin and, therefore, they can be used for the treatment of chronic and acute pancreatitis by virtue of their trypsin-inhibiting activity or for the treatment of hemorrhagic diseases and thrombosis by virtue of their plasmin- and thrombin-inhibiting activities.

The compounds of the present invention are given in an amount of about 5 to 1,000 mg/day, preferably about 10 to 500 mg/day, to adult patients at least once a day either orally or parenterally, though the dose is not particularly limited, since it varies depending on the kind of diseases, extent of symptoms, age of the patient, physical conditions, body weight, kind of concomitant treatments, if any, frequency of the treatment and intended effects. Particularly in the treatment of pancreatitis, the dose is within the above-mentioned range, preferably about 10 to 500 mg/day and more preferably about 30 to 300 mg/day, for adults.

The dosage forms of the compounds of the present invention include, for example, powders, fine granules, granules, tablets, capsules, suppositories and injections. These pharmaceutical preparations are produced by an ordinary process by using an ordinary pharmaceutical carrier.

Namely, in the production of an oral solid preparation, an excipient and, if necessary, a binder, disintegrator, lubricant, colorant, corrigent, etc. are added to the active ingredient and the mixture is shaped into tablets, coated tablets, granules, powders or capsules.

Examples of the excipients include lactose, corn starch, sucrose, glucose, sorbitol, crystalline cellulose and silicon dioxide. Examples of the binders include polyvinyl alcohol, polyvinyl ether, ethylcellulose, methylcellulose, acacia gum, tragacanth, gelatin, shellac, hydroxypropylcellulose, hydroxypropylstarch and polyvinylpyrrolidone. Examples of the disintegrators include starch, agar, gelatin powder, crystalline cellulose, calcium carbonate, sodium hydrogencarbonate, calcium citrate, dextrin and pectin. Examples of the lubricants include magnesium stearate, talc, polyethylene glycol, silica and hardened vegetable oils. The colorants are those permitted to be added to medicines. Examples of the corrigents include cocoa powder, menthol, aromatic powder, peppermint oil, borneol and cinnamon powder. These tablets and granules may be coated suitably with sugar, gelatin, etc., if necessary.

In the preparation of the injection, a pH-controlling agent, buffering agent, stabilizer, solubilizer, etc. are added, if necessary, to the active ingredient to form an intravenous injection in an ordinary manner.

The following examples will further illustrate the present invention, which by no means limit the invention.

EXAMPLE 1

4-(2-Hydroxyethylthio)phenyl 4-guanidinobenzoate methanesulfonate:

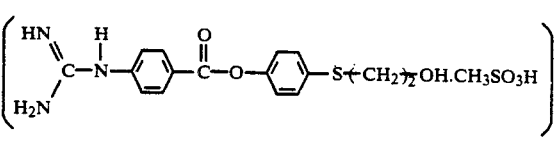

(1) Synthesis of 2-hydroxyethyl 4-hydroxyphenyl sulfide:

280 ml of 28% aqueous ammonia was added to a mixture of 50 g of 4-hydroxythiophenol and 54.56 g of ethylene bromohydrin and the mixture was stirred vigorously at room temperature for 2 h. 225 m( of concentrated hydrochloric acid was added thereto under cooling with ice to adjust the pH of the aqueous phase to 1. After extraction with ethyl acetate, the ethyl acetate layer was washed with a saturated aqueous common salt solution and then dried over anhydrous magnesium sulfate. The resulting solution was filtered and the filtrate was concentrated and subjected to silica gel column chromatography to obtain 44.77 g (yield: 66%) of the intended compound having the following physical properties:

m.p.: 70°–71(°C.)
N.M.R. spectra δ (DMSO-d₆)
2.89(t, J=7.2Hz, 2H),
3.60(td, J=7.2, 6.4Hz, 2H),
4.08(t, J=6.4Hz, 1H),
6.73(d, J=8.4Hz, 2H),
7.23(d, J=8.4Hz, 2H), 9.00(s, 1H)

(2) Synthesis of 4-hydroxyphenyl 2-(tetrahydropyran-2-yloxy)ethyl sulfide 17.91 g of 2-hydroxyethyl 4-hydroxyphenyl sulfide prepared by the above process (1) was dissolved in 280 m( of tetrahydrofuran. 0.18 g of p-toluenesulfonic acid was added to the solution. A solution of 17.69 g of 3,4-dihydro-2H-pyran in 140 ml of tetrahydrofuran was added dropwise to the mixture under cooling with ice and then the mixture was stirred at room temperature for 4 h. The solvent was distilled off and the residue was extracted with diethyl ether, washed with an aqueous sodium hydrocarbonate solution and dried over anhydrous magnesium sulfate. The resulting solution was filtered and the filtrate was concentrated and subjected to silica gel column chromatography to obtain 15.38 g (yield: 58%) of the intended compound having the following physical properties:

N.M.R. spectra δ (DMSO-d₆)
1.1~1.85(m, 6H),
2.96(t, J=7.6Hz, 2H), 3.1~3.9(m, 4H),
4.53(bs, 1H), 6.74(d, J=9.6Hz, 2H),
7.24(d, J=9.6Hz, 2H), 9.52(bs, 1H)

(3) Synthesis of 4-(2-hydroxyethylthio)phenyl 4-guanidinobenzoate methanesulfonate:

96.08 g of 4-hydroxyphenyl 2-(tetrahydropyran-2-yloxy)ethyl sulfide synthesized by the above process (2) was dissolved in 800 m( of pyridine. 4-Guanidinobenzoyl chloride was added to the solution under cooling with ice and the mixture was stirred at room temperature for 24 h or longer. A saturated aqueous sodium hydrocarbonate solution was added thereto under cooling with ice and the precipitate thus obtained was recovered by filtration, washed with water, then acetone and finally ethyl acetate and dried to obtain 104 g of 4-(2-tetrahydropyran-2-yloxyethylthio)phenyl 4-guanidinobenzoate carbonate.

This product was suspended in 1033 m( of methanol and 37.9 g of methanesulfonic acid was added to the suspension. After methanesulfonic acid was substantially dissolved, 31 g of active carbon was added to the solution and stirred for 30 min and the active carbon was filtered off. 1.2 l of ether was added to the filtrate under cooling with ice and the mixture was left to stand overnight. The crystals thus formed were recovered by filtration and dissolved again in 1.2 l of methanol under heating. The solution was treated with active carbon and the active carbon was removed by filtration. 2.5 l of diethyl ether was added to the filtrate and the mixture was left to stand for 30 min. The crystals thus formed were recovered by filtration to obtain 35.44 g (yield: 22%) of the intended compound having the following physical properties:

m.p.: 141°–143(°C.)
N.M.R. spectra δ (DMSO-d₆)
2.36(s,3H), 3.06(t, J=6.8 Hz, 2H),
3.58(t, J=6.8 Hz, 2H),
7.23(d, J=8.8 Hz, 2H), 7.4~7.47(m, 4H),
7.77(bs, 3H), 8.15(d, J=8.4 Hz, 2H),
10.09(bs, 1h)

EXAMPLE 2

4-(2-Succinimidoethylthio)phenol 4-guanidinobenzoate methane sulfonate:

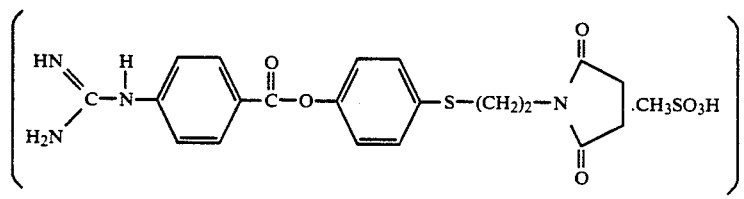

(1) Synthesis of 1-bromo-2-succinimidoethane:

49.5 g of succinamide was dissolved in 750 ml of 2-butanone under heating. 187.9 g of dibromoethane and 138 g of anhydrous potassium carbonate were added to the solution and the mixture was heated under reflux for 9.5 h.

Then, inorganic matter was removed by filtration and the filtrate was distilled. 2 l of chloroform was added to the distillation residue and the mixture was washed with water. The organic layer was dried over anhydrous magnesium sulfate and filtered. The filtrate was distilled and then purified to obtain 67.37 g (yield: 65%) of the intended compound having a boiling point of 127° C./2.5 mmHg.

(2) Synthesis of 4-hydroxyphenyl 2-succinimidoethyl sulfide 175.92 g of 1-bromo-2-succinimidoethane obtained by the above process (1) and 107.6 g of 4-hydroxythiophenol were dissolved in 860 mg of ethanol. 141.42 g of anhydrous potassium carbonate was added to the solution and the mixture was heated under reflux for 4 h. After completion of the reaction, inorganic matter was removed by filtration and the solvent was distilled out. Water was added to the residue and the pH of the mixture was controlled to 1 with hydrochloric acid. The resulting mixture was extracted with ethyl acetate and the ethyl acetate layer was washed with water and dried over anhydrous magnesium sulfate. After filtration, the filtrate was distilled and the residue was recrystallized from ethyl acetate to obtain 42.67 g (yield: 20%) of the intended compound having the following physical properties:

m.p.: 114°–122.5° C.
N.M.R. spectra δ (DMSO-d₆)
2.52(s, 4H), 2.91(t, J=8.0 Hz, 2h),
3.50(t, J=8.0 Hz, 2H), 6.73(d, J=9.6 Hz, 2H),
7.24 (d, J=9.6 Hz, 2h), 9.57 (bs, 1H)

(3) Synthesis of 4-(2-succinimidoethylthio)phenyl 4-guanidinobenzoate methanesulfonate 32.04 g of 4-hydroxyphenyl 2-succinimidoethyl sulfide obtained by the above process (2) was dissolved in 260 ml of pyridine. 4-guanidinobenzoyl chloride was added to the solution under cooling with ice and the mixture was stirred at room temperature for 16.5 h. After completion of the reaction, 5 l of a saturated aqueous solution of sodium hydrocarbonate was added thereto under cooling with ice. A precipitate thus formed was recovered by filtration, washed with water and then acetone, and dried to obtain 45.5 g (yield: 75%) of 4-(2-succinimidoethylthio)phenyl 4-guanidinobenzoate carbonate.

Then, this product was suspended in 910 ml of methanol. 12.0 g of methanesulfonic acid was added to the suspension and the mixture was heated to obtian a solution. The methanolic solution was concentrated to form crystals, which were recovered by filtration to obtian 37.6 g (overall yield: 58%) of the intended compound having the following physical properties:
m.p.: 201.6° C.
N.M.R. spectra δ (DMSO-d$_6$):

which was concentrated and cooled. Diethyl ether was added thereto to precipitate an oil, which was washed with diethyl ether twice. The oil was dissolved in methanol. Ethyl acetate was added to the solution and a precipitate thus formed was recovered by filtration to obtain 1.94 g of the intended compound having the following physical properties:
m.p.: 129°-130° C.
N.M.R. spectra δ(DMSO-d$_6$)
1.10(t, J=7.6 Hz, 3h), 2.38(s, 3H),
3.15(t, J=6.4 Hz, 2H),
3.44(q, J=7.6 Hz, 2H),
3.56(t, J=6.4 Hz, 2h),
7.21(d, J=9.6 Hz, 2h),
7.41(d, J=9.6 Hz, 2H),
7.45(d, J=9.6 Hz, 2H), 7.76(bs, 4h),
8.14(d, J=9.6 Hz, 2h), 10.10(bs, 1H)

EXAMPLE 4

4-(2-Phthalminidoethylthio)phenyl 4-quanidinobenzoate methanesulfonate

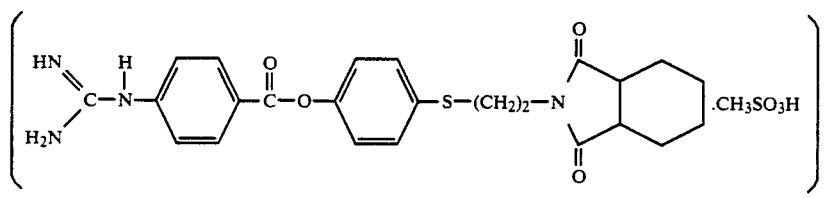

2.36(s, 3h), 2.53(s, 4H),
3.15(t, J=6.8 Hz, 2H),
3.61(t, J=6.8 Hz, 2H),
7.27(d, J=8.8 Hz, 2H),
7.43(d, J=8.8 Hz, 2H),
7.47(d, J=8.8 Hz, 2H),
7.7(bs, 4H), 8.16(d, J=8.8 Hz, 2H),
10.10(bs, 1H)

EXAMPLE 3

4-(2-Ethoxyethylthio)phenyl 4-guanidinobenzoate methansulfonate

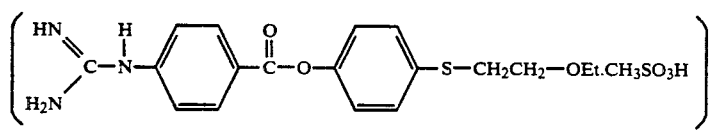

3.4 g of 2-ethoxyethyl 4-hydroxyphenyl sulfide was dissolved in 50 ml of pyridine. 4-Guanidinobenzoyl chloride was added to the solution under cooling with ice and the mixture was stirred at room temperature for 27 h. A saturated aqueous solution of sodium hydrocarbonate was added thereto under cooling with ice. A precipitate thus formed was recovered by filtration, washed with water and then with acetone, and dried to obtian 2.86 g (yield: 405) of 4-(2-ethoxyethylthio)phenyl 4-guanidinobenzoate carbonate.

This product was suspended in 100 ml of methanol. 0.78 g of methanesulfonic acid was added to the suspension and the mixture was heated to obtain a solution, (1) Synthesis of 1-brome-2-phthalimidoethane The intended compound having the following physical property was synthesized by the process (1) of Example 2 and purified by means of silica gel column chromatography (yield: 66%).
melting point: 81.5° to 82.5° C.

(2) Synthesis of 4-hydroxyphenyl 2-phthalimidoethyl sulfide

The intended compound having the following physical properties was synthesized by the process (2) of Example 2 and purified by means of silica gel column chromatography (yield: 92%):
m.p.: 125°-126.5° C.
N.M.R. spectra δ (DMSO-d$_6$)
3.03(t, J=7.6Hz, 2H),
3.67(t, J=7.6 Hz, 2H), 6.62(d, J=9.2 Hz, 2H),
7.18(d, J=9.2 Hz, 2H),
9.45(s, 1h)

(3) Synthesis of 4-(2-phthalimidoethylthio)phenyl 4-guanidinobenzoate methanesulfonate The intended compound having the following physical properties was synthesized by the process (4) of Example 2

N.M.R. spectra δ (DMSO-d$_6$):
2.39(s, 3H), 3.24(t, J=6.8 Hz, 2H)
3.79(t, J=6.8 Hz, 2H),
7.12(d, J=9.6 Hz, 2H),
7.35(d, J=9.6 Hz, 2H),
7.40((d, J=9.6 Hz, 2H), 7.7(bs, 4H),
7.76(s, 4H), 8.06(d, J=9.6 Hz, 2H),
10.03(s, 1H)

EXAMPLE 5

The following compounds were synthesized by the same process as in Example 2:

4-(3-succinimidopropylthio)phenyl 4-guanidinobenzoate methanesulfonate

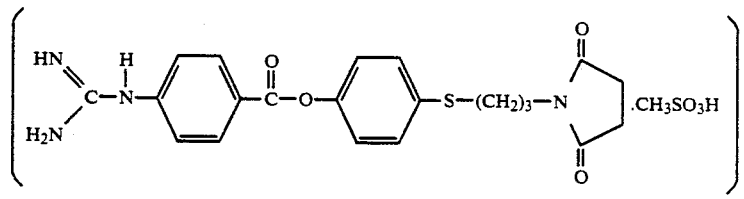

N.M.R. spectra δ (DMSO-d$_6$): 1.76(quint, J=8.0 Hz, 2H), 2,41(s, 3H), 2.62(s, 4H) 2.95(t, J=8.0 Hz, 2H), 3.50(t, J=8.0 Hz, 2H), 7.22(d, J=9.6 Hz, 2H), 7.43(d, J=9.6 Hz, 4H), 7.78(bs, 4H), 8.15(d, J=9.6 Hz, 2H), 10.12(bs, 1H)

4-(4-succinimidobutylthio)phenyl 4-guanidinobenzoate methanesulfonate:

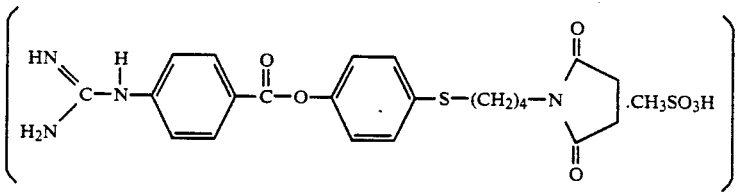

m.p.: 151.5~153.5
N.M.R. spectra δ (DMSO-d$_6$):
1.35~1.8(m, 4H), 2.36(s, 3H), 2.60(s, 4H), 2.59(t, J=6.4 Hz, 2H), 3.38(t, J=6.4 Hz, 2H) 7.22(d, J=9.6 Hz, 2H), 7.44(d, J=9.6 Hz, 4H), 7.9(bs, 4H), 8.15(d, J=9.6 Hz, 2H), 10.12(bs, 1h)

4-(5-succinimidopentylthio)phenyl 4-guanidinobenzoate methanesulfonate

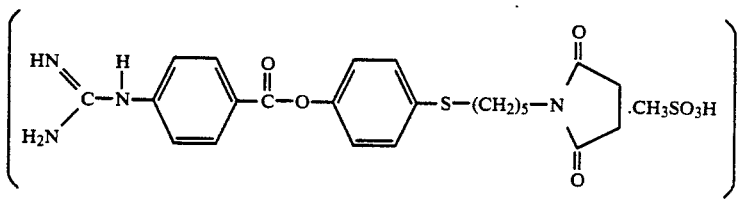

N.M.R. spectra δ (DMSO-d$_6$):
7.22(d, J=9.6 hz, 2H), 7.44(d, J=9.6 Hz, 4H), 7.9(bs, 4H), 8.15(d, J=9.6 Hz, 2H), 10.12(bs, 1H)

4-(5-succinimidopentylthio)phenyl 4-guanidinobenzoate methanesulfonate

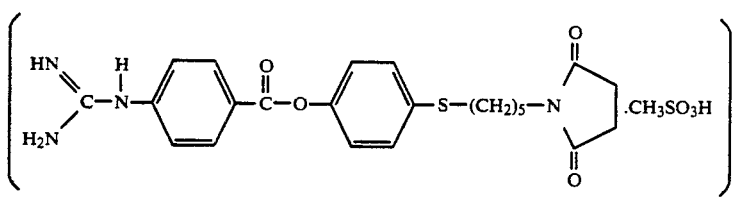

N.M.R. spectra δ (DMSO-$d_6$):
1.2~1.8(m, 6H), 2.39(s, 3H),
2.61(s, 4H),, 2.96(t, J=8.0 Hz, 2H),
3.34(t, J=8.0 Hz, 2H),
7.22(d, J=10.0 Hz, 2H),
7.42(d, J=10.0 Hz, 4H),
7.78(bs, 4H), 8.15(d, J=10.0 Hz, 4H), 10.12(s, 1H)

4-[2-(cis-1,2-cyclohexanedicarboxylimido)ehtylthio]-phenyl 4-guanidinobenzoate methanesulfonate

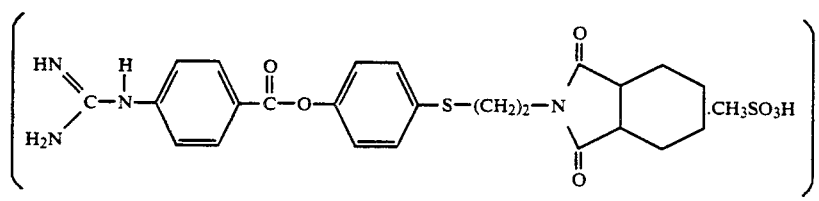

N.M.R. spectra δ (DMSO-$d_6$):
1.2~1.85(m, 8H), 2.38(s, 3H),
2.76~2.97(m, 2H),
3.17(bt, J=7.2 Hz, 2H),
3.61(bt, J=7.2 Hz, 2H),
7.25(d, J=10.0 Hz, 2H),
7.43(d, J=10.0 Hz, 2H),
7.48(d, J=10.0 Hz, 2H), 7.76(bs 4H),
8.16((d, J=10.0 Hz, 2H), 10.11(s, 1H)

4-[2-(5,5-dimethyl-2,4-dioxooxazolidin-3-yl)ethylthio]-phenyl 4-guanidinobenzoate methanesulfonate

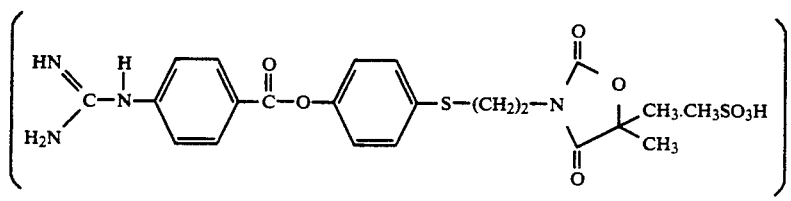

N.M.R. spectra δ (DMSO-$d_6$):
1.46(s, 6H), 2.32(s, 3H), 3.24(t, J=6.8 Hz, 2H),
3.60(t, J=6.8 Hz, 2H),
7.18(d, J=10.0 Hz, 2H), 7.35(d, J=10.0 Hz, 2H),
7.42(d, J=10.0 Hz, 2H),
7.66(bs, 4H), 8.07((d, J=10.0 Hz, 2H),
9.96(bs, 1H)

We claim:
1. A guanidinobenzoic ester compound of the formula:

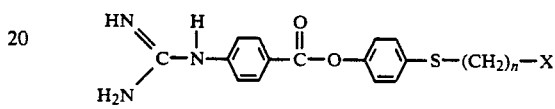

wherein X represents a group of the formula:

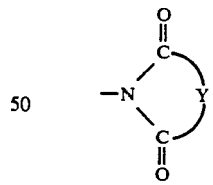
(1)

in which Y is a group of the formula: —$(CH_2)_m$—, m being an integer of 3,

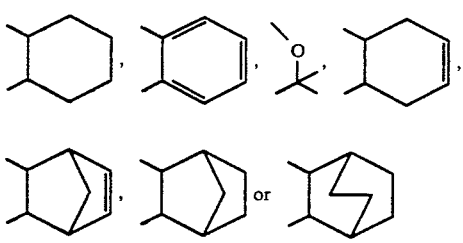

and n represents an integer of 1 to 5, and pharmacologically acceptable salt thereof.

2. Guanidinobenzoic ester compounds according to claim 1 wherein X represents a group of the formula:

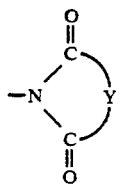

in which Y is a group of the formula: $-(CH_2)_m-$, m being an integer of 3,

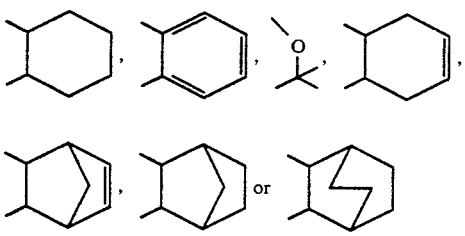

3. Guanidinobenzoic ester compounds and pharmacologically acceptable salts of them according to claim 1, wherein X represents a group of the formula:

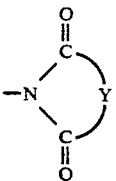

in which Y is a group of the formula: $-(CH_2)_m-$, m being an integer of 3,

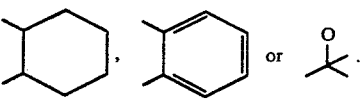

4. Guanidinobenzoic ester compounds and pharmacologically acceptable salts of them according to claim 1, wherein n is 2 to 5.

5. Guanidinobenzoic ester compounds and pharmacologically allowable salts of them according to claim 1, wherein n represents 2 to 5 and X represents a group of the formula:

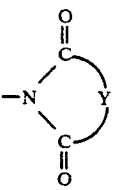

in which Y is a group of the formula: $-(CH_2)_m-$, m being an integer of 3,

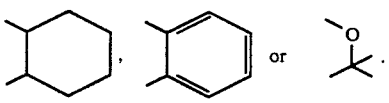

6. Guanidinobenzoic ester compounds and pharmacologically allowable salts of them according to claim 1, wherein n represents an integer of 2.

7. Guanidinobenzoic ester compounds and pharmacologically allowable salts of them according to claim 1, wherein n represents an integer of 2 and X represents a group of the formula:

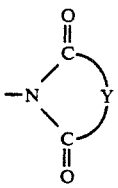

in which Y is a group of the formula: $-(CH_2)_m-$, m being an integer of 3,

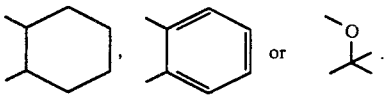

8. Guanidinobenzoic ester compounds and pharmacologically allowable salts of them according to claim 1, wherein n represents an integer of 2 to 5 and X represents a group of the formula:

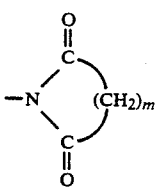

m being an integer of 3.

9. A guanidinobenzoic ester derivative or its pharmacologically allowable salt according to claim 1, wherien the compound is 4-(20phthalimidoethylthio)phenyl 4-guanidinobenzoate.

10. A guanidinobenzoic ester derivative or its pharmacologically allowable salt according to claim 1, wherein the compound is 4-[2-(cis-1,2-cyclohexanedicarboxyimido)ethylthio]phenyl 4-guanidinobenzoate.

11. A guanidinobenzoic ester derivative or its pharmacologically allowable salt according to claim 1, wherein the compound is 4-[2-(5,5-dimethyl-2,40dioxooxazolidin-3-yl)ethylthio]phenyl 4-guanidinobenzoate.

* * * * *

UNITED STATES PATENT AND TRADEMARK OFFICE
CERTIFICATE OF CORRECTION

PATENT NO.   : 5 075 335
DATED        : December 24, 1991
INVENTOR(S)  : Shigeru SOUDA et al It is certified that error appears in the above-identified patent and that said Letters Patent is hereby corrected as shown below:

Column 17, line 13; change "and" (last occurrence) to
---or a---.
    line 39; after the formulas insert "and pharmacologically acceptable salts thereof."
Column 18, line 57; change "wherien" to ---wherein---.
    line 58; change "4-(20phthalimidoethylthio)" to ---4-(2-phthalimidoethylthio)---.
    line 66; change "2,40diox-" to ---2,4-diox- ---.

Signed and Sealed this

Sixth Day of April, 1993

*Attest:*

STEPHEN G. KUNIN

*Attesting Officer*   Acting Commissioner of Patents and Trademarks